United States Patent [19]

Hindley et al.

[11] 4,080,474

[45] Mar. 21, 1978

[54] HYPOLIPIDAEMIC COMPOSITIONS

[75] Inventors: Richard Mark Hindley, Reigate; Keith Howard Baggaley, Redhill, both of England

[73] Assignee: Beecham Group Limited, England

[21] Appl. No.: 769,219

[22] Filed: Feb. 16, 1977

Related U.S. Application Data

[62] Division of Ser. No. 655,870, Feb. 6, 1976.

[30] Foreign Application Priority Data

Feb. 19, 1975  United Kingdom ................ 6909/75

[51] Int. Cl.$^2$ ..................... A01N 9/24; C07C 49/84

[52] U.S. Cl. ................................... 424/331; 424/333; 424/337; 424/340; 260/590 R; 260/592; 260/600 R; 260/521 R; 260/516; 260/501.17; 260/501.19; 260/558 S; 260/559 R; 260/558 H; 260/308 D; 260/609 R; 260/613 R; 260/611 A; 260/465 F; 560/17; 560/61; 424/269; 424/304; 424/308; 424/317

[58] Field of Search ............... 260/590 R, 590 D, 592; 424/331

[56] References Cited

U.S. PATENT DOCUMENTS

| | | | |
|---|---|---|---|
| 3,458,565 | 7/1969 | Bicking et al. | 260/590 R |
| 3,557,148 | 1/1971 | Moed et al. | 260/590 R |
| 3,997,608 | 12/1976 | Suh | 260/590 R |
| 4,001,339 | 1/1977 | Chodnekar et al. | 424/331 |

Primary Examiner—James O. Thomas, Jr.
Assistant Examiner—James H. Reamer
Attorney, Agent, or Firm—Jacobs & Jacobs

[57] ABSTRACT

Allyloxy benzoic acid derivatives have hypolipidaemic activity, compositions for controlling or reducing serum lipid level in mammals, novel substituted phenoxy and phenylthio allyl compounds and administration of the compositions to mammals in need thereof.

29 Claims, No Drawings

HYPOLIPIDAEMIC COMPOSITIONS

This is a division of Ser. No. 655,870, filed Feb. 6, 1976.

This invention relates to pharmaceutical compositions which have hypolipidaemic activity, and in particular to compositions comprising phenoxy allyl compounds.

Occlusive vascular disease is characterised by an accumulation of lipids (especially cholesterol, triglycerides and phospholipids) in the interior of large arteries. These lesions obstruct the vessel and result in ischemia of the organ supplied by the artery. Prolonged or sudden ischemia arising in this way is a major cause of death in many countries. It have been demonstrated that increased levels of lipids, for example chlolesterol, in the blood is related to an increased prevalence of coronary artery disease and heart attack; and there is thus a demand for a drug which effectively reduces serum lipid levels.

In our W. German Offenlegungsschrift No. 2439458, there is described a pharmaceutical composition which comprises one or more pharmaceutically acceptable carriers together with a compound of formula (I):

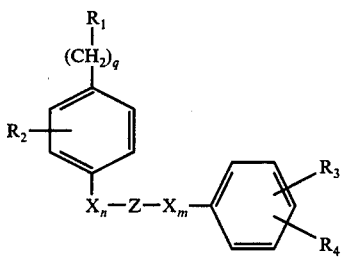

wherein:
$R_1$ is a carboxylic acid group or a group capable of being converted in the human body to a carboxylic acid group;
$R_2$ is a hydrogen atom, a lower alkyl group or a lower alkoxyl group;
$R_3$ is a hydrogen or halogen atom, or a lower alkyl or lower alkoxyl group;
$R_4$ is a hydrogen or halogen atom, or a phenyl, lower alkyl, lower alkoxyl, halc-lower alkyl, nitro or carboxylic ester group; or $R_3$ and $R_4$ together form the residue of a benzene ring;
Z is oxygen or sulphur;
X is a straight or branched lower alkylene, lower alkyleneoxy, lower-alkylene-thio, or lower-alkylene-carbonyl group;
$q$ is 0 or an integer from 1–12; and one of $m$ and $n$ is 0 and the other is 1.

We have now found a class of substituted phenoxy (or phenylthio) allyl compounds, individual members of the class having useful hypolipidaemic activity.

Although certain benzene derivatives substituted by inter alia alkenyloxy or alkenylthio groups have been disclosed as having pharmacological activity, usually anti-inflammatory or analgesic properties (see for example, Belgian Pat. Nos. 621,225 and 718,573, French Pat. Nos. 1,580,970, 2,054,532 and 2,108,943, and U.S. Pat. Nos. 3,586,713 and 3,824,277), we are not aware of any literature which suggests the present specific class of allyloxy and allylthio benzenes or that such compounds may possess hypolipidaemic activity.

Accordingly the present invention provides a pharmaceutical composition comprising at least one pharmaceutically acceptable carrier, together with a compound of formula (II):

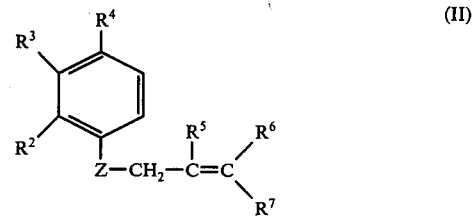

wherein
one of the groups $R^2$, $R^3$ and $R^4$ represents a group $-(CH_2)_qR^1$, and the remaining groups $R^2$, $R^3$ and $R^4$ are hydrogen;
$R^1$ is a carboxylic acid group or a pharmaceutically acceptable non-toxic salt, ester, amide or hydrazide of a carboxylic acid group; an alkyl group optionally substituted by one or more hydroxyl or lower alkoxy groups; cyano, formyl, acyl, carboxyl-substituted acyl group or tetrazole group;
$q$ is 0 or an integer from 1 to 12;
Z is oxygen or sulphur; and
$R^5$, $R^6$ and $R^7$ are independently hydrogen or a lower alkyl group.

When used herein, the adjective "lower" means that the alkyl part of the group to which it applies contains from 1 to 6 carbon atoms.

Suitable lower alkyl groups for $R^5$, $R^6$ and $R^7$ in formula (II) include methyl, ethyl and straight and branched chained propyl and butyl groups.

Preferably $R^5$ is hydrogen.

A compound with $R^6$ and $R^7$ groups different and the corresponding compound with these groups interchanged will, of course, be geometrical isomers of each other. It is to be understood that the present invention includes both such cis- and trans- isomers as well as mixtures thereof.

When the group $R^1$ is a salt of a carboxylic acid group, suitable salts include metal salts e.g. aluminum, alkali metal salts such as sodium or potassium, alkaline earth metal salts such as calcium or magnesium, and ammonium or substituted ammonium salts for example those with lower alkylamino such as triethylamine, hydroxy-lower alkylamines such as 2-hydroxyethylamine, bis-(2-hydroxyethyl)-amine or tri-(2-hydroxyethyl)-amine, cycloalkylamines such as bicyclohexylamine, or with procaine, dibenzylamine, N,N-dibenzylethylenediamine, 1-ephenamine, N-ethylpiperidine, N-benzyl-β-phenethylamine, dehydroabietylamine, N,N'-bis-dehydroabietylethylenediamine, or bases of the pyridine type such as pyridine, collidine or quinoline.

Preferred salts are the sodium and potassium salts.

Suitable ester groups include alkyl, aryl and aralkyl esters, for example $C_{1-20}$ straight or branched chain alkyl esters. Lower alkyl and lower aralkyl esters are preferred, such as methyl, ethyl, straight and branched chain propyl, butyl, pentyl, hexyl and benzyl esters.

Suitable alkyl groups for the group $R^1$ include straight and branched $C_{1-20}$ alkyl groups, preferably lower alkyl groups in particular methyl. Any such alkyl group may be substituted at any position with a hydroxy or lower alkoxy group.

Preferred such substituted-alkyl groups include hydroxymethyl, methoxymethyl, ethoxymethyl.

Suitable acyl groups include alkanoyl groups, preferably lower alkanoyl for example acetyl.

On especially useful group of compounds for use in the compositions of this invention is represented by formula (III):

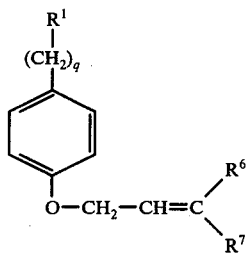

wherein $R^1$, $R^6$, $R^7$ and $q$ are as defined in relation to formula (II).

For a compound to have maximum potential as a hypolipidaemic agent, it must significantly decrease serum lipid levels and have little or no effect on growth, liver weight and liver lipid. Within compounds of formula (III) such a combination of parameters are best satisfied when either $R^1$ is a carboxylic acid group or a salt, or ester thereof when $q$ is 0; or $R^1$ is methyl, hydroxymethyl or a carboxylic acid group or a salt or ester thereof when $q$ is an integer from 1 to 12.

Another group of compounds having good hypolipidaemic activity and useful in the compositions of this invention is represented by formula (IV):

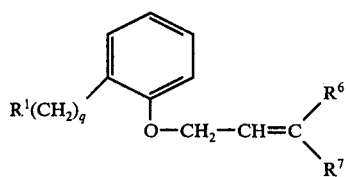

wherein $R^1$, $R^6$, $R^7$ and $q$ are as defined above with respect to formula (II).

Preferred compounds of formula (I) include those wherein $q$ is 0 and $R^1$ is a carboxyl group or a salt, or ester thereof.

A further sub-class of compounds useful for incorporation in the present compositions have formula (I):

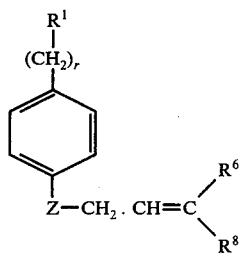

wherein $R^1$, Z and $R^6$ are as defined with respect to formula (II), $r$ is an integer from 1 to 12 and $R^8$ is a lower alkyl group.

The integer $r$ may conveniently be from 2 to 6.

Preferably $r$ is 2 when $R^1$ is a carboxylic acid group or a salt or alkyl ester thereof.

The compositions may be formulated for administration by any route, although an oral administration is preferred. The compositions may be in the form of tablets, capsules, powders, granules, lozenges, or liquid preparations, such as oral or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinyl-pyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups, or elixirs, or may be presented as dry products for reconstitution with water or other suitable vehicle before use. Such liquid preparations may contain conventional additives such as suspending agents, for example sorbitol, syrup, methyl cellulose, glucose syrup, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

Suppositories will contain conventional suppository bases, e.g. cocoa, butter or other glyceride.

For parenteral administration, fluid unit dosage forms are prepared utilizing the compound and a sterile vehicle, water being preferred. The compound, depending on the vehicle and concentration used, can be either suspended or dissolved in water for injection and filter sterilized before filling into a suitable vial or ampoule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an acccompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration. Where the compositions comprise dosage units, each unit will preferably contain from 50mg – 1g of the active ingredient. The dosage as employed for adult human treatment will preferably range from 100mg to 5g per day, for instance 1500 mg. per day, depending on the route and frequency of administration.

Also included with the scope of the present invention is a method for controlling or reducing the serum lipid levels of mammals, including man, which method comprises the administration to the mammal of one or more compounds of the formula (II) above. An oral administration is preferred.

Some of the compounds of formula (II) are novel compounds. Thus, the present invention also provides compounds of formula (II) above wherein either, i. $q$ is 0, 1, or 2, $R^1$ is cyano and $R^2$ to $R^7$ and Z are as defined with respect to formula (II); or ii. $q$ is an integer from 2 to 12, $R^1$ is a carboxylic acid group or a pharmaceutically acceptable non-toxic salt, ester, amide or hydrazide thereof, an alkyl group optionally substituted by one or more hydroxyl or lower alkoxy groups, a cyano, formyl, acyl, or carboxyl-substituted acyl group; and Z and $R^2$ to $R^7$ are as defined with respect to formula (II) except that when Z is oxygen, and $q$ is 2, then $R^1$ is not a carboxyic acid group.

One class of novel compounds has the formula:

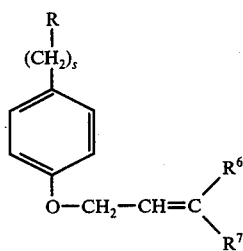

wherein R is a lower alkyl group or a carboxylic acid ester group, $s$ is an integer from 2 to 6 and $R^6$ and $R^7$ are as defined with respect to formula (II).

Specific novel compounds include the following:

ethyl 3-[4-(3-methyl-but-2-enyloxy)phenyl]-propionate;
4-(but-2-enyl-1-oxy)-benzylethyl ether;
ethyl 3-[4'-(but-2-enyl-1-oxy)-phenyl]-propionate;
ethyl 2-(but-2-enyl-1-oxy)-benzoate;
ethyl 4-(but-2-enyl-1-oxy)-phenyl acetate;
4-(but-2-enyl-1-oxy)-benzonitrile;
2-(but-2-enyl-1-oxy)-acetophenone;
3-(but-2-enyl-1-oxy)-acetophenone;
4-(but-2-enyl-1-oxy)ethylbenzene;
iso-propyl 3-[4'-(but-2-enyl-1-oxy)-phenyl]-propionate;
4-[4'-(but-2-enyl-1-oxy)-phenyl]-butan-2-one;
ethyl 2-(but-2-enyl-1-thio)-benzoate;
benzyl 3-[4'-(but-2-enyl-1-oxy)-phenyl]-propionate;
n-hexyl 3-[4'-(but-2-enyl-1-oxy)-phenyl]-propionate;
3-[4'-(but-2-enyl-1-oxy)-phenyl]-propionic acid;
4'-(but-2-enyl-1-oxy)-benzoic acid;
sodium 3-[4'-(but-2-enyl-1-oxy)-phenyl]-propionate;
sodium 4'-(but-2-enyl-1-oxy)-benzoate;
3-[4'-(but-2-enyl-1-oxy)-phenyl]-propionayl hydrazide;
4-(but-2-enyl-1-oxy)-acetophenone;
ethyl 4-(but-2-enyl-1-thio)-benzoate;
ethyl 3-[4'-(but-2-enyl-1-oxy)-phenyl]-propionate;
ethyl 3-[4'-(hept-2-enyl-1-oxy)-phenyl]-propionate;

The compounds of the present invention may be prepared by the reaction of a compound of the formula (VI):

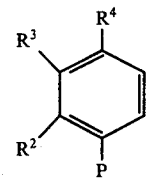

with a compound of formula (VII):

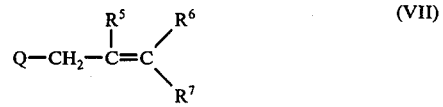

wherein one of the groups P or Q is —ZH (where Z is defined with reference to formula (II)) or a reactive derivative thereof, and the other is a readily displaceable group and wherein $R^2$, $R^3$, $R^4$, $R^5$, $R^6$ and $R^7$ are as defined with reference to formula (II) above, and optionally thereafter converting the group $R^1$ within the substituent $R^2$, $R^3$ or $R^4$ to a different such group $R^1$.

The resultant product of formula (II) may then be combined with a pharmaceutically acceptable carrier to produce the novel compositions of the invention.

Reactive deritives of the group —ZH include salts and other derivatives which increase the nucleophilicity of the atom Z.

By a "readily displaceable group" is meant an atom or group displaceable by a nucleophilic centre (such as the lone pair electrons on a hydroxyl oxygen or alkoxide ion). Such groups include halides such as I, Br or Cl; pseudo-halides such as the azido group $N_2$—; active esters such as the groups $O.SO_2CH_2$. $O.CO.OC_2H_5$; compounds prepared in situ from dehydrating agents such as carbodiimides or carbonyldiimidazoles, phosphorus pentachloride, phosphoryl chloride, thionyl chloride, phosphorus pentoxide or sulphuric acid; or other such good leaving groups.

For the preparation of compounds wherein Z is oxygen the group —ZH is a hydroxyl group. If the hydroxyl compound used in the above condensation reaction is in the form of a salt, it is generally in the form of the sodium or potassium salt.

When the condensation reaction uses a salt as one of the reactants, the salt is preferably produced by means of a strong base, for example, sodium hydride, sodamide, or a sodium alkoxide or sodium methoxide. Suitable solvents for the reaction include dimethylformamide or dimethylsulphoxide (especially when employing sodium hydride or sodamide or base methanol (when using sodium methoxide) and ethanol (when using sodium ethoxide).

Alternatively the free hydroxyl group in compound (VI) or (VII) may be employed and the process is then carried out in the presence of an acid acceptor, for example a tertiary organic base such as pyridine, triethylamine or N-methylpyrrolidine; or potassium carbonate (in acetone as solvent).

For the preparation of compounds of formula (II) wherein Z is sulphur the group —ZH is a thiol group. Such a group may be used in the above condensation either as the free thiol or as a salt thereof.

It may be preferable to modify the group $R^1$ within substituents $R^2$, $R^3$ and/or $R^4$ after the condensation reaction rather than before. Thus, it is preferable, when preparing compounds of formula (II) wherein $R^1$ includes an amide or carboxylic acid group, first to prepare the corresponding compound with a carboxylic acid ester group and then to convert such group to a carboxylic acid group or amide by conventional means. It may be noted that some of the compounds wherein $R^1$ is an alkyl ester are difficult to hydrolyse to the corresponding carboxylic acid group and it is often convenient to prepare the benzyl ester by the above condensation, which ester is more readily hydrolysed.

Similarly, if the group $R^1$ contains a hydroxyl group, it may be advantageous to first protect it by forming a readily hydrolysable ester which can be removed subsequent to the condensation reaction.

Alternative methods of preparing compounds wherein $R^1$ contains an ester group include the esterification of the free acid or its salt or other reactive derivative of the acid, or transesterification or a compound having a different ester group. Esterification may be performed by any conventional method, for example by reaction of the free acid: (a) with the appropriate alcohol in the presence of a catalyst such as a strong acid, dry hydrogen chloride, or p-toluenesulphonic acid; or (b) with the appropriate halide or sulphate of the alcohol in the presence of dimethylsulphoxide and calcium carbonate or with the halide in the presence of hexamethylphosphoramide or (c) by phase transfer catalysis methods with the halide and/or sulphate of the alcohol in aqueous and/or organic solution in the presence of a quaternary ammonium salt such as tetrabutyl ammonium bisulphate or halide, or benzyl-trimethylammonium halide.

The formation of compounds (II) wherein $R^1$ is an ester may also be carried out by conventional transesterification methods, for example, reaction of an ester with the appropriate second alcohol in the presence of a catalyst such as the sodium salt of the alcohol, or dry hydrogen chloride, p-toluenesulphonic acid, or potassium cyanide.

Compounds of formula (II) wherein $R^1$ is an ester may also be prepared by alkanolysis of the corresponding nitrile $R^1$ is C≡N); or by hydrolysis of an iminoether compound having formula (II) wherein $R^1$ is a group of formula:

wherein $R_x$ is the hydrocarbon residue of an alcohol or phenol.

Compounds wherein $R^1$ contains a carboxylic acid group can also be prepared by the acid or base catalysed hydrolysis of the corresponding compound of formula (II) wherein $R^1$ is selected from:
 a. carboxylic acid amide group;
 b. nitrile group (—C≡N);
 c. esterified carboxylic acid group.

Hydrolysis of amides may be carried out using a mineral acid as catalyst, suitably hydrochloric acid or sulphuric acid. Base catalysed hydrolysis may be carried out using an alkali metal or alkaline earth metal hydroxide, e.g. sodium or potassium hydroxide. Suitably the hydrolysis reaction is carried out in aqueous solution and fairly severe reaction conditions are preferred, e.g. refluxing for several hours. The desired compound can be isolated as the free acid by neutralisation of the resultant reaction mixture or as the appropriate base addition salt (e.g. sodium salt if sodium hydroxide was employed) or acid addition salt (e.g. the hydrochloride if HCl was employed). Alternatively the free acid can be converted to any desired salt by standard procedures.

For the hydrolysis of a compound wherein $R^1$ is a nitrile group ammonia is liberated and thus the preferred catalyst is an acid which will bind the ammonia e.g. a hydrogen halide such as HCl or HBr. If base catalysed hydrolysis is used, ammonia is liberated and the acid will be obtained as an alkali salt or, after neutralisation, as the free acid.

For the hydrolysis of an esterified carboxylic acid group, preferably the process involves hydrolysis with a strong base such as sodium hydroxide. The esterified carboxylic acid groups $R^1$ may be, for example, lower alkoxycarbonyl groups such as methoxycarbonyl or tertiary butoxycarbonyl groups. The remarks made earlier about salts of the resultant free acid also apply in this case.

A further method for the preparation of compounds of formula (II) wherein $R^1$ is a carboxylic acid group comprises the carbonation of a compound of formula (II) wherein $R^1$ is a group of formula:

—MX followed by hydrolysis, wherein M is magnesium, calcium or lithium and X is chlorine, bromine or iodine. Such reagents are of course well known in the art and may be prepared by known methods. Carbonation is preferably carried out using gaseous carbon dioxide but solid carbon dioxide may be used on occasion. Hydrolysis of the intermediate formed after carbonation can be carried out simply by the addition of water.

Compounds of formula (II) wherein $R^1$ is a hydroxymethyl group may be prepared by reduction of the compound wherein $R^1$ is a formyl or ester group, for example with sodium borohydride.

Compounds wherein $R^1$ contains a carboxyl group may be prepared by oxidation of the corresponding precursor having formula (II) wherein $R^1$ is selected from:
 a. formyl;
 b. methyl;
 c. hydroxymethyl;
 d. acyl.

Examples of the reagents which may be employed to effect such oxidations include respectively,
 a. basic silver oxide, or concentrated nitric acid;
 b. acidic sodium or potassium dichromate;
 c. manganese dioxide followed by basic silver oxide;
 d. a hypohalite. The acyl group may be an acetyl group (CH$_3$CO). Preferably the hypohalite reactant is sodium hypohalite which may be generated in situ in aqueous solution by the reaction of sodium hydroxide on a mixture of iodine and potassium iodide.

The desired free acid may be isolated and converted to any desired salt by known methods.

Compounds of formula (II) wherein $R^5$ and $R^6$ are both hydrogen, and in a cis-configuration may be prepared by hydrogenation of the corresponding acetylene of formula (VIII):

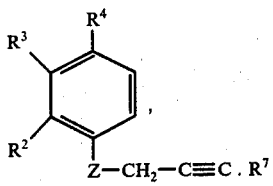
(VIII)

wherein $R^2$, $R^3$, $R^4$, $R^7$ and Z are as hereinbefore defined.

Suitably, catalytic hydrogenation in the presence of palladium on barium sulphate may be employed.

Compounds of the invention may also be prepared by reacting a compound of formula (IX) or (X) with a compound of formula (XI) or reacting a compound of formula (XII) with a compound of formula (XIII) or (XIV).

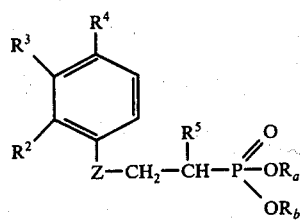
(IX)

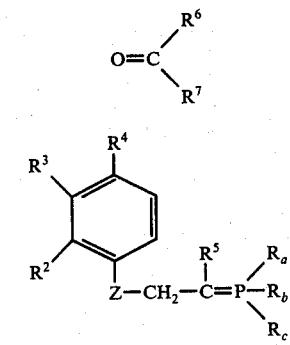
(XI)
(X)

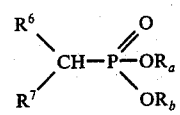
(XIII)

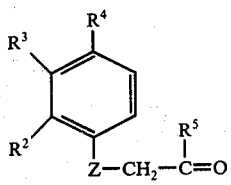
(XII)

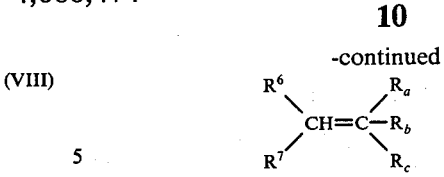
(XIV)

wherein the symbols $R^2 - R^7$ and Z are as defined with respect to formula (II) and $R_a$, $R_b$ and $R_c$ are the same or different and each is lower alkyl, aryl or aralkyl.

The reaction is usually carried out in an inert solvent such as dimethylformamide at a temperature of from about 10° to about 100° C. Under these conditions the reaction proceeds smoothly over a period of from a few minutes to a few hours and the product may be isolated by any of the usual techniques e.g. solvent evaporation or anti-solvent precipitation followed by filtration. In many cases the reaction may be carried out in a solvent in which the product is insoluble and in such cases the precipitated solid may be collected by filtration. Purification of the product may be by any of the usual chromatographic or recrystallisation techniques.

During the preparation of the starting materials (IX) (X), (XI), (XII), (XIII), or (XIV), and indeed the end product (II) it may be desirable to protect any particularly reactive groups present. Thus, free carboxylic acid groups are preferably protected by esterification; free amino groups may be protected using the groups known for that purpose in peptide synthesis.

The following Examples illustrate the invention.

In these Examples, the products which can exist as geometrical isomers are a mixture of cis- and trans-isomers unless specified otherwise.

EXAMPLE 1

Ethyl-3-[4-((3-methyl-but-2-enyloxy)-phenyl)]-propionate

Sodium (1.6g., 0.07m) was dissolved in absolute ethanol (50 ml) with protection from atmospheric moisture. To this was added a solution of ethyl-3-(4-hydroxyphenyl)-propionate (9.7g., 0.05mole) in absolute ethanol (25 ml) and the mixture stirred 30 minutes at room temperature. 1-Bromo-3-methyl-but-2-ene (6.7g., 0.05 mole) in absolute ethanol (25 ml) was added dropwise to the stirred solution and the mixture was boiled under reflux with stirring for 6 hours. The mixture was cooled, the inorganic salts filtered and washed with cold ethanol (30 ml) and the filtrate evaporated. The residue was dissolved in dichloromethane (150 ml), washed twice with 5% sodium hydroxide solution (100 ml), once with water (100 ml), dried over anhydrous magnesium sulphate to give 8.01g of crude product. This was distilled to give ethyl-3-[4-((3-methyl-but-2-enyloxy)-phenyl)]-propionate (5.0g., 38%) boiling at 178°–182° C (3mm).

Example 2 – 15

The following compounds were also prepared by the method of Example 1.

| Example No. | | Yield % | b.p. (or m.p.)° C |
|---|---|---|---|
| 2. | Ethyl 3-[4-(3-methylbut-2-enyl-1-oxy)]-benzoate | 45 | 148° at 0.7 mm |
| 3. | 4-(But-2-enyl-1-oxy)-benzylethyl ether | 39 | 125 – 8 at 1.0 mm |
| 4. | 4-(But-2-enyl-1-oxy)-toluene | 38 | 90 – 93 at 1.5 mm |
| 5. | 2-(But-2-enyl-1-oxy)-toluene | 29 | 71 – 4 at 0.2 mm |
| 6. | Ethyl 4-(prop-2-enyl-1-oxy)-benzoate | 43 | 156 at 10 mm |
| 7. | Ethyl 4-(prop-2-enyl-1-oxy)-phenyl acetate | 32 | 126 – 7 at 0.5 mm |
| 8. | Ethyl 3-[4'-(but-2-enyl-1-oxy)-phenyl]-propionate | 52 | 168 – 72 at 2 mm |
| 9. | Ethyl 4-(but-2-enyl-1-oxy)-benzoate | 36 | m.p. 51 – 2° C |
| 10. | Ethyl 2-(but-2-enyl-1-oxy)-benzoate | 39 | — |
| 11. | Ethyl 3-(but-2-enyl-1-oxy)-benzoate | 42 | — |
| 12. | Ethyl 2-(prop-2-enyl-1-oxy)-benzoate | 35 | 153 at 13 mm |
| 13. | Ethyl 4-(prop-2-enyl-1-oxy)-benzoate | 46 | 88 at 0.1 mm |

Example 2 – 15-continued

The following compounds were also prepared by the method of Example 1.

| Example No. | | Yield % | b.p. (or m.p.)° C |
|---|---|---|---|
| 14. | Ethyl 4-(but-2-enyl-1-oxy)-phenyl acetate | 37 | — |
| 15. | Ethyl 3-[4'-(prop-2-enyl-1-oxy)-phenyl]-propionate | — | — |

Nmr, data for the compounds of Examples 10, 11, 14 and 15:

(8.37g.). This was distilled under reduced pressure to give trans-ethyl-3-[4'-(but-2-enyl-1-oxy)phenyl]-propionate (6.19g., 50%), boiling at 153°–155° C (0.5mm).

Examples 17 – 30

The following compounds were also prepared by the method of Example 16.

| Example No. | | Yield % | m.p./b.p. ° C |
|---|---|---|---|
| 17. | 4-(But-2-enyl-1-oxy)-benzonitrile | 72 | m.p. 65–7 |
| 18. | 2-(But-2-enyl-1-oxy)-benzaldehyde | 40 | 115–7 at 0.7mm |
| 19. | 3-(But-2-enyl-1-oxy)benzaldehyde | 27 | 118–20 at 0.8mm |
| 20. | 2-(But-2-enyl-1-oxy)-acetophenone | 52 | 129–32 at 2.5mm |
| 21. | 3-(But-2-enyl-1-oxy)-acetophenone | 58 | 126–30 at 0.6mm |
| 22. | 4-(But-2-enyl-1-thio)-toluene | 47 | 100–6 at 1mm |
| 23. | 4-(But-2-enyl-1-oxy)ethylbenzene | 42 | 97–8 at 0.9mm |
| 24. | Trans-iso-propyl-3-[4'-(but-2-enyl-1-oxy)-phenyl]-propionate | 40 | 150–51 at 0.2mm |
| 25. | Trans-4-[4'-(but-2-enyl-1-oxy)-phenyl]-butan-2-one | 53 | 144–7 at 0.6mm |
| 26. | Trans-ethyl-2-(but-2nenyl-1-thio)-benzoate | 73 | 132–3 at 0.7mm |
| 27. | Trans-benzyl-3-[4'-but-2-enyl-1-oxy)-phenyl]-propionate | 40 | — |
| 28. | n-Hexyl-3-[4'-(but-2-enyl-1-oxy)-phenyl]-propionate | 43 | 200–5 at 2.5mm |
| 29. | 4-[3-Methyl-but-2-enyl-1-oxy]-benzaldehyde | 63 | 133–6 at 1mm |
| 30. | Trans-ethyl-4-(hex-2-enyl-1-oxy)-benzoate | 73 | 159–60 at 0.4mm |

| Example No. | δ (ppm) | |
|---|---|---|
| 10. | 7.98–6.81 | (4H, aromatic, complex) |
| | 5.81 | (2H, =CH, m) |
| | 4.54 | (2H, —OCH$_2$, m) |
| | 4.37 | (2H, —OCH$_2$, ester, q) |
| | 1.76 | (3H, —CH$_3$, d) |
| | 1.39 | (3H, —CH$_3$ ester, t) |
| 11. | 7.84–6.96 | (4H, aromatic, complex) |
| | 5.80 | (2H, =CH—, m) |
| | 4.50 | (2H, —OCH$_2$, d) |
| | 4.38 | (2H, —OCH$_2$ ester, q) |
| | 1.83 | (2H, —CH$_2$, d) |
| | 1.39 | (3H, —CH$_3$, t) |
| 14. | 7.20 ⎫ | (4H, aromatic, aa' bb') |
| | 6.88 ⎭ | |
| | 5.78 | (2H, =CH, m) |
| | 4.41 | (2H, —OCH$_2$, m) |
| | 4.13 | (2H, OCH$_2$ ester, q) |
| | 3.52 | (2H, —CH$_2$—, s) |
| | 1.78 | (3H, —CH$_3$, d) |
| | 1.24 | (3H, —CH$_3$ ester, t) |
| 15. | 7.12 ⎫ | (4H, aromatic, aa' bb') |
| | 6.80 ⎭ | |
| | 5.98 | (1H, =CH, m) |
| | 5.29 | (2H, =CH$_2$, t) |
| | 4.49 | (2H, —OCH$_2$, d) |
| | 4.12 | (2H, —OCH$_2$ ester, q) |
| | 2.72 | (4H, —CH$_2$, m) |
| | 1.21 | (3H, —CH$_3$ ester, t) |

EXAMPLE 16

Trans-Ethyl-3-[4'-(but-2-enyl-1-oxy)-phenyl]-propionate

Anhydrous potassium carbonate (10g., 0.07m) was suspended in acetone (80 ml), ethyl-3-(4'-hydroxyphenyl)-propionate (9.2g., 0.05m) was added and the mixture was stirred at room temperature while trans-1-bromobut-2-ene (6.65g., 0.05m), dissolved in acetone (40 ml) was added dropwise. The mixture was boiled under reflux with stirring for 4 hours, cooled to room temperature, filtered under suction and the solvent removed under vacuum. The residue was dissolved in ether (100 ml) and washed twice with 5% sodium hydroxide solution (100 ml), once with water (100 ml) and dried over anhydrous magnesium sulphate. Filtration and evaporation of the solvent gave the crude product (8.37g.). This was distilled under reduced pressure to give trans-ethyl-3-[4'-(but-2-enyl-1-oxy)phenyl]-propionate (6.19g., 50%), boiling at 153°–155° C (0.5mm).

EXAMPLE 31

3-[4'-(but-2-enyl-1-oxy)-phenyl]-propionic acid

Ethyl-3-[4'-(but-2-enyl-1-oxy)-phenyl]-propionate (48g., 0.194m) was dissolved in absolute alcohol (100 ml) and a solution of sodium hydroxide (10g., 0.25m) in water (100 ml) was added. The mixture was boiled under reflux for 18 hours, cooled and extracted twice with dichloromethane (100 ml). The aqueous layer was acidified with 10% hydrochloric acid and the product filtered and dried under vacuum at 65° C. Crystallisation from 20% aqueous ethanol gave 3-[4'-(but-2-enyl-1-oxy)-phenyl]-propionic acid (27.36g., 64%) melting at 107°–8° C.

EXAMPLE 32

4'-(But-2-enyl-1-oxy)-benzoic acid was prepared by the method of Example 31, crystallised from 30% aqueous ethanol, yield 81%, m.p. 173°–5° C.

EXAMPLE 33

Sodium 3-[4'-(but-2-enyl-1-oxy)-phenyl]-propionate

3-[4'-(but-2-enyl-1-oxy)-phenyl]-propionic acid (4.40g., 0.02m) was suspended in water (20 ml) and sodium bicarbonate (1.68g., 0.02m) in water (10 ml) was added. The mixture was heated on a steam bath for 1 hour and the water removed under vacuum. The last traces of water were removed by azeotropic distillation with ethanol and then trituration of the residue with acetone. The acetone suspension was filtered and the product dried under vacuum at 60° C to give analytically pure sodium-3-[4'-(but-2-enyl-1-oxy)-phenyl]-propionate (4.26g., 88%) melting at 284°–285° C.

EXAMPLE 34

Sodium-4'-(but-2-enyl-1-oxy)-benzoate was prepared by the method described in Example 33, yield 88%. m.p. >300° C.

EXAMPLE 35

3-[4'-(but-2-enyl-1-oxy)-phenyl]-propionylhydrazide

Ethyl-3-[4'-(but-2-enyl-1-oxy)-phenyl]-propionate (5g., 0.02m) was dissolved in absolute ethanol, hydrazine (20 ml of 40% solution) was added and the mixture was boiled under reflux for 6 hours. The mixture was allowed to stand at room temperature overnight and was then diluted with water (100ml). The solid product was filtered off, dried under vacuum at 60° C and crystallised from ethanol to give 3-[4'-(but-2-enyl-1-oxy)-phenyl]-propionylhydrazide (4.33g., 93%) melting at 125°–127° C.

EXAMPLE 36

5-[4'-(But-2-enyl-1-oxy)-phenyl]-tetrazole 4-(But-2-enyl-1-oxy)-benzonitrile (8.65g., 0.05m), sodium azide (3.75g., 0.051m) and ammonium chloride (7.5g., 0.15m) were mixed in dry dimethylformamide and heated at 115° C with stirring for 36 hours. The mixture was cooled to room temperature, the solvent removed under vacuum, the residue suspended in water (100 ml) and acidified to pH2 using concentrated hydrochloric acid. The product was filtered off, dried, and crystallised from absolute ethanol to give 5-[4'-(but-2-enyl-1-oxy)phenyl]-tetrazole (8.32g., 77%) melting at 214°–216° C.

EXAMPLE 37

Methyl-3-[4'-(but-2-enyl-1-oxy)phenyl]-propionate

Ethyl-3-[4'-(but-2-enyl-1-oxy)-phenyl]-propionate (5.0g., 0.02m) was dissolved in a solution of sodium (0.5g) in methanol (150 ml). The mixture was boiled under reflux for 5 hours, cooled and the solvent removed under vacuum. Water (50 ml) was added to the residue and the product extracted twice with dichloromethane (50 ml). The organic extracts were dried (MgSO$_4$) and evaporated to give the crude methyl ester (4.94g). This was distilled to give methyl-3-[4'-(but-2-enyl-1-oxy)-phenyl]-propionate (4.48g., 96%) boiling at 142°–145° C (0.3mm).

EXAMPLE 38

4-(But-2-enyl-1-oxy)-acetophenone

4-Hydroxyacetophenone (13.6g., 0.1m) was dissolved in dry dimethylformamide (50 ml) in a 3-necked flask equipped with a stirrer, dropping funnel and condenser with a calcium chloride drying tube. Sodium hydride (3.0g., of 80% suspension in paraffin, 0.1m) was added portionwise with stirring and stirred at 50° C until the reaction ceased. The mixture was cooled to room temperature and a solution of 1-bromo-but-2-ene (13.5g., 0.1m) dissolved in dimethylformamide (20 ml) was added dropwise with stirring. The mixture was stirred 2 hours at room temperature, 1 hour on a steam bath, cooled to room temperature and then added to iced water (100 ml). The product was extracted into ether (2 × 100 ml), washed twice with 5% sodium hydroxide solution (100 ml), once with water (100 ml) dried (MgSO$_4$), and evaporated. The product was distilled to give 4-(but-2-enyl-1-oxy)-acetophenone (10.43., 55%) boiling at 149°–152° C (1.5mm).

EXAMPLE 39

4-(But-2-enyl-1-oxy)-benzaldehyde was prepared by the method described in Example 38, yield 61%, b.p. 124°–6° C at 0.9mm.

EXAMPLE 40

Trans-Ethyl-4-(but-2-enyl-1-thio)-benzoate

Diethyl-4,4'-dithiobisbenzoate (8.30g., 0.023m) was dissolved in absolute ethanol (275 ml) at room temperature and sodium borohydride (1.83g., 0.048m) was added to the stirred solution, then stirred at room temperature for 90 minutes during which time the solution turned yellow. A solution of trans-1-bromo-but-2-ene (6.21g., 0.046m) in ethanol (20 ml) was added and the mixture stirred at room temperature for 3 hours. After this time the solvent was removed under reduced pressure, the residue dissolved in ether, washed with 10% aqueous sodium carbonate (50 ml), water (100 ml) and brine (100 ml) dried (MgSO$_4$) and evaporated to give a pale yellow oil which crystallised on standing. Crystallisation from 40–60 petrol gave trans-ethyl-4-(but-2-enyl-1-thio)-benzoate (4.60g., 43%) as colourless leaflets. M.p. 41°–42° C.

EXAMPLE 41 a. Ethyl-3-[4'-(but-2-ynyl-1-oxy)-phenyl]-propionate

Sodium (2.4g., 0.104m) was dissolved in absolute ethanol (80 ml) with protection from atmospheric moisture and to this was added a solution of ethyl-3-(4-hydroxyphenyl)-propionate (20.6g., 0.106m) in ethanol (20 ml). The mixture was stirred at room temperature for 30 minutes and treated dropwise with a solution of but-2-ynyl-methanesulphonate (12.5g., 0.08m) in ethanol (20 ml). The mixture was boiled under reflux 3 hours with stirring, cooled, filtered and the solvent removed under vacuum. The product was diluted with water (100 ml), extracted into ether, washed twice with 5% sodium hydroxide solution (100 ml), once with water (100 ml), dried (MgSO$_4$) and evaporated to give the crude product (19g). Distillation of the product gave ethyl-3-[4'-(but-2-ynyl-1-oxy)-phenyl]-propionate (8.66g., 44%) boiling at 162°–166° C (2mm).

b. cis-Ethyl-3-[4'-(but-2-enyl-1-oxy)-phenyl]-propionate

Ethyl-3-[4'-(but-2-enyl-1-oxy)-phenyl]-propionate (4.1g., 0.0167m) is methanol (30 ml) in the presence of 5% palladium on barium sulphate (0.15g) and quinoline (0.35ml) was hydrogenated at atmospheric pressure until exactly one equivalent of hydrogen (375 ml) had been absorbed. The catalyst was filtered off under vacuum, the solvent evaporated and the product dissolved in ether (50 ml). The ether solution was washed twice with 5% hydrochloric acid (50 ml), once with saturated sodium bicarbonate solution (50 ml) and once with water (50 ml), dried (MgSO$_4$) and evaporated. The crude product was distilled to yield cis-ethyl-3-[4'-(but-2-enyl-1-oxy)-phenyl]-propionate (3.43g., 83%) boiling at 146°–150° C (1.5mm).

EXAMPLE 42

Prepared similarly to Example 41, were
a. Ethyl-3-[4'-(hept-2-ynyl-1-oxy)phenyl]-propionate (Yield 61%, b.p. 176° C at 1.6mm).
b. cis-Ethyl-3-[4'-(hept-2-enyl-1-oxy)-phenyl]-propionate (Yield 94%, b.p. 182°–4° at 2.5 mm).

EXAMPLE 43

4-[3-Methyl-but-2-enyl-1-oxy]-benzyl alcohol 4-(3-Methyl-but-2-enyl-1-oxy)-benzaldehyde (7.6g., 0.04m) was dissolved in ethanol (100 ml); sodium borohydride (0.4g., 0.012m) added and the mixture boiled under reflux for 1 hour. The mixture was cooled, the solvent removed under vacuum, the product dissolved in dichloro-methane (100 ml), washed with water (100 ml), dried ($MgSO_4$) and evaporated to give 5.92g of crude product Pure 4-[3-methyl-but-2-enyl-1-oxy]-benzyl alcohol (2.3g., 31%) m.p. 42° C was obtained by chromatography on silica gel in dichloromethane.

Biological Data

The hypocholesterolaemic and/or hypotriglyceridaemic effects of several compounds of the present invention were demonstrated in the following experiment:

Groups of 8 male albino rates (C.F.Y. strain), weighing approximately 150 g., were given a powdered commercially available diet (oxoid) to which compounds were added at level of 0.25%. These diets were fed for 7 days. The rats were then killed and their serum total cholesterol and triglyceride were measured by the Technicon Autoanalyser.

Table 1 shows the results expressed in terms of percentage cholesterol lowering and percentage triglyceride lowering compared with controls.

Table 1
[N.S. = not significant]

| Compound of Example No. | % Reduction Cholesterol | % Reduction Triglycerides |
|---|---|---|
| 1 | 14.8 | 48.9 |
| 2 | 20.0 | 53.4 |
| 3 | 21.4 | 43.0 |
| ;11 4 | 19.3 | N.S. |
| 6 | 21.3 | 32.6 |
| 7 | 21.8 | N.S. |
| 8 | 13.0 | 54.0 |
| 9 | 32.2 | 59.4 |
| 10 | 19.0 | 27.0 |
| 12 | 14.1 | 28.4 |
| 14 | 13.1 | 40.5 |
| 15 | 23.0 | 47.0 |
| 16 | N.S. | 26.5 |
| 18 | 19.3 | 31.3 |
| 19 | 19.3 | 29.9 |
| 20 | N.S. | 23.3 |
| 21 | N.S. | 22.1 |
| 22 | N.S. | 19.8 |
| 23 | N.S. | 25.6 |
| 27 | 9 | 56 |
| 29 | 4 | N.S. |
| 30 | N.S. | 51 |
| 31 | 20.7 | 43.3 |
| 32 | 25.0 | 48.0 |
| 34 | 28.2 | 46.0 |
| 37 | 7 | 40 |
| 39 | 30.9 | N.S. |
| 41 | 12 | 13 |
| 42 | N.S. | 35.8 |

We claim:

1. A compound of the formula:

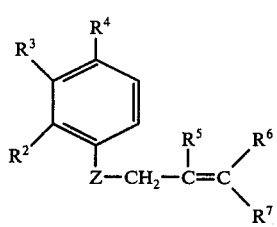

wherein
one of the groups $R^2$, $R^3$ and $R^4$ is —$(CH_2)_qR^1$ in which $q$ is 2 to 12 and $R^1$ is lower alkanoyl and the remaining groups $R^2$, $R^3$ and $R^4$ are hydrogen;
Z is oxygen or sulphur; and
$R^5$, $R^6$ and $R^7$ are each independently hydrogen or lower alkyl.

2. A compound according to claim 1 wherein Z is oxygen.

3. A compound according to claim 1 wherein $R^5$ is hydrogen.

4. A compound according to claim 1 wherein Z is oxygen and $R^5$ is hydrogen.

5. A compound according to claim 1 of the formula:

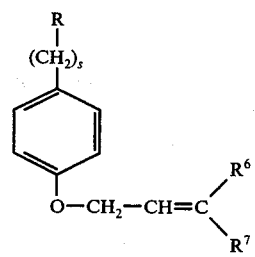

wherein
R is lower alkanoyl;
$s$ is an integer from 2–6; and $R^6$ and $R^7$ are hydrogen or lower alkyl.

6. A compound according to claim 5 wherein R is acetyl.

7. A pharmaceutical composition for controlling or reducing serum lipid level comprising at least one pharmaceutically acceptable carrier, together with as active hypolipidaemic ingredient an effective amount of a compound of the formula:

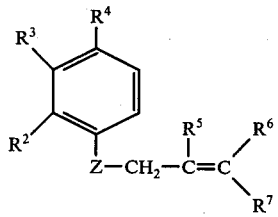

wherein
one of the groups $R^2$, $R^3$ and $R^4$ is —$(CH_2)_qR^1$ in which $q$ is 0 or an integer from 1 to 12 and $R^1$ is lower alkanoyl, and the remaining groups $R^2$, $R^3$ and $R^4$ are hydrogen;
Z is oxygen or sulphur; and
$R^5$, $R^6$ and $R^7$ are each independently hydrogen or lower alkyl.

8. A composition according to claim 7 wherein Z in the compound is oxygen.

9. A composition according to claim 7 wherein $R^5$ in the compound is hydrogen.

10. A composition according to claim 7 wherein Z in the compound is oxygen and $R^5$ in the compound is hydrogen.

11. A composition according to claim 7 wherein the active hypolipidaemic ingredient is a compound of the formula:

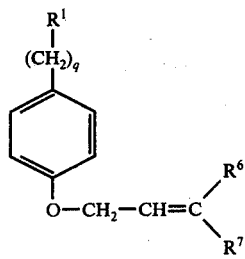

and $R^1$, $R^6$, $R^7$ and $q$ are as defined in claim 7.

12. A composition according to claim 11 wherein $R^1$ is acetyl.

13. A composition according to claim 7 wherein $R^1$ is acetyl and $q$ is an integer from 1 to 12.

14. A composition according to claim 7 wherein the active hypolipidaemic ingredient is a compound of the formula:

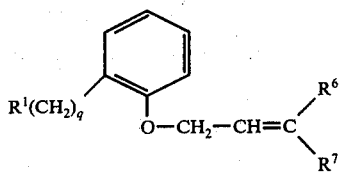

and $R^1$, $R^6$, $R^7$ and $q$ are as defined in claim 7.

15. A composition according to claim 7 wherein the active hypolipidaemic ingredient is a compound of the formula:

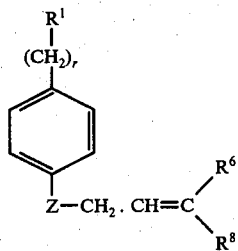

and $R^1$, $Z$ and $R^6$ are as defined in claim 34, $r$ is an integer from 1 to 12 and $R^8$ is lower alkyl.

16. A composition according to claim 15 wherein $r$ is an integer from 2 to 6.

17. A composition according to claim 15 wherein $R^1$ is acetyl.

18. A method for controlling or reducing serum lipid level in a mammal in need thereof which comprises administering to the mammal an effective hypolipidaemic amount of a composition according to claim 7.

19. A method according to claim 18 wherein the administration is oral.

20. A method for controlling or reducing serum lipid level in a mammal in need thereof which comprises administering to the mammal an effective hypolipidaemic amount of a composition according to claim 8.

21. A method for controlling or reducing serum lipid level in a mammal in need thereof which comprises administering to the mammal an effective hypolipidaemic amount of a composition according to claim 9.

22. A method for controlling or reducing serum lipid level in a mammal in need thereof which comprises administering to the mammal an effective hypolipidaemic amount of a composition according to claim 10.

23. A method for controlling or reducing serum lipid level in a mammal in need thereof which comprises administering to the mammal an effective hypolipidaemic amount of a composition according to claim 11.

24. A method for controlling or reducing serum lipid level in a mammal in need thereof which comprises administering to the mammal an effective hypolipidaemic amount of a composition according to claim 12.

25. A method for controlling or reducing serum lipid level in a mammal in need thereof which comprises administering to the mammal an effective hypolipidaemic amount of a composition according to claim 13.

26. A method for controlling or reducing serum lipid level in a mammal in need thereof which comprises administering to the mammal an effective hypolipidaemic amount of a composition according to claim 14.

27. A method for controlling or reducing serum lipid level in a mammal in need thereof which comprises administering to the mammal an effective hypolipidaemic amount of a composition according to claim 15.

28. A method for controlling or reducing serum lipid level in a mammal in need thereof which comprises administering to the mammal an effective hypolipidaemic amount of a composition according to claim 16.

29. A method for controlling or reducing serum lipid level in a mammal in need thereof which comprises administering to the mammal an effective hypolipidaemic amount of a composition according to claim 17.

* * * * *